United States Patent [19]

Hansen

[11] Patent Number: 4,596,643

[45] Date of Patent: Jun. 24, 1986

[54] CIS-TRANS ISOMERIZATION OF OLEFINIC COMPOUNDS BY PHOTOINDUCED CATALYSIS

[75] Inventor: Steven G. Hansen, Arden, N.C.

[73] Assignee: Olin Corporation, Cheshire, Conn.

[21] Appl. No.: 720,895

[22] Filed: Apr. 8, 1985

[51] Int. Cl.[4] .............................................. B01J 19/12
[52] U.S. Cl. ............................. 204/157.15; 204/157.9
[58] Field of Search ........................ 204/158 R, 162 R

[56] References Cited

U.S. PATENT DOCUMENTS 4,338,173 7/1982 Yardley ........................... 204/162 R

OTHER PUBLICATIONS

Schmidt et al, The Journal of Chemical Physics, vol. 51, No. 5, Sep. 1969, pp. 2024–2034.
Chem. Abstracts, vol. 80, p. 3671g (1974).
Chem. Abstracts, vol. 83, p. 97637n, p. 113665c (1975).
Chem. Abstracts, vol. 94, p. 102544p (1981).
Chem. Abstracts, vol. 95, p. 150958u (1981).
Chem. Abstracts, vol. 100, p. 144806y (1984).

*Primary Examiner*—Howard S. Williams
*Attorney, Agent, or Firm*—William A. Simons; Thomas P. O'Day

[57] ABSTRACT

Method of isomerizing an olefin by photoinduced catalysis utilizing COS and a photosensitizer therefor. The invention is particularly applicable for the isomerization of nerol to geraniol.

26 Claims, No Drawings

CIS-TRANS ISOMERIZATION OF OLEFINIC COMPOUNDS BY PHOTOINDUCED CATALYSIS

FIELD OF THE INVENTION

The present invention relates to an improvement in methods for effecting cis-trans isomerization of olefinic compounds by photoinduced catalysis.

BACKGROUND OF THE INVENTION

Many chemical reactions are enhanced by irradiation with light of various wavelengths. There are two principal mechanisms by which light may affect chemical reactions. In the type often referred to as photosensitization, a molecule is irradiated with light and attains a relatively long-lived excited state which is then capable of collisionally transfering its energy to a reactant species. The energy transferred to the reactant species causes the latter to change its reactivity, i.e., to chemically react with another reactant species, to dissociate, etc. The role of this type of molecule, conventionally termed a photosensitizer, is primarily to absorb light and transfer the energy generated thereby to a reactant species. A photosensitizer is usually a much stronger absorber of the irradiated light than the species to which it transfers its energy. A photosensitizer permits reactions to occur which otherwise would be difficult or impossible due to the fact that the reactant species absorbs too little light to cause appreciable reaction.

In the other type of reaction, commonly referred to as photoinduced catalysis, a catalytically active species is created by absorption of light. Certain molecules are known to decompose to or become converted to catalytically active species when irradiated with light of certain wavelengths. In this type of reaction, the agent responsible for inducement of the intended reaction is a true catalyst in the process rather than a mere transferor of energy.

It is known (Schmidt et al, J. Chem. Phys., Vol. 51(5), pp. 2024-34 (1969)) that the direct photo excitation of carbonyl sulfide (COS) produces an active catalyst species which will efficiently induce the cis-trans isomerization of olefinic compounds. Schmidt et al theorize that atomic sulfur in its ground electronic state and in an excited electronic state is generated by the photolysis of COS and that the sulfur product of the photolysis acts as the catalytic species for the cis-trans isomerization of olefinic compounds.

A disadvantage in this process, however, is that COS is difficult to directly excite. Thus, COS does not absorb in the near UV wavelengths. The longest wavelength at which COS absorbs is about 270 nm, with maximum absorption occurring at 220 nm. This gives rise to several disadvantages in connection with utilizing this procedure to isomerize olefinic compounds. For example, light sources for this range are generally more expensive and less efficient producers of photons than those which yield longer wavelengths. Moreover, direct excitation of COS is often hindered by olefin absorption of light of shorter wavelengths. Olefin absorption is undesirable in that it wastes energy and may induce unwanted photolysis or side reactions. It would be highly advantageous to extend the wavelength range at which photolysis of COS occurs in order to enable the utilization of less expensive light sources, increase the efficiency of the cis-trans isomerization and to reduce unwanted side reactions.

It is an object of the present invention to provide an improvement in the method for effecting the cis-trans isomerization of olefinic compounds by photo-induced catalysis utilizing COS.

SUMMARY OF THE INVENTION

The above and other objects are realized by the present invention which provides an improvement in a method of effecting isomerization of a cis- or trans-olefinic compound or mixture thereof by photoinduced catalysis to the photostationary state with respect to the ratio of the cis-isomer to the trans-isomer wherein the catalytic species capable of catalyzing the isomerization is produced by the indirect photolysis of COS, the improvement comprising effecting the photolysis of COS in the presence of a photosensitizer for the production of the catalytic species, the photosensitizer comprising a compound capable of absorbing light of wavelengths above about 250 nm and thereafter collisionally dissociating COS to produce the catalytic species.

DETAILED DESCRIPTION OF THE INVENTION

The present invention is predicated on the discovery that the inclusion of a photosensitizer for the photolysis of COS greatly enhances the efficiency of the olefinic compound isomerization. The improved isomerization reaction of the invention, in essence, comprises an amalgamation of the two basic types of photocatalysis, namely, photosensitization and photo-induced catalysis.

Although not wishing to be bound by any theory as to the mechanism for the isomerization reaction, it is hypothesized that the energy accumulated by the sensitizer as a result of absorption of light collisionally effects decomposition of the COS to the active species. Thus, the active catalytic species is generated not only by direct photolysis of the COS, but also, by photosensitization.

Numerous advantageous improvements in the basic isomerization reaction are provided by the inclusion of a photosensitizer in the reaction. Thus, the useful wavelength range for triggering the catalytic reaction is extended. The utilization of sensitizers which absorb light at wavelengths above 250 nm enables initiation of the isomerization reaction with longer wavelength light than that utilized in the basic photolysis reaction carried out in the absence of a photosensitizer. Such longer wavelengths are less likely to be absorbed by the olefinic compound and, therefore, less likely to cause unwanted side reactions or to waste photons.

Moreover, by extending the wavelength range, cheaper and more efficient light sources can be utilized for the reaction. The utilization of a photosensitizer permits the optical density of the reaction mixture to be increased regardless of the UV wavelength chosen. Since more light can be absorbed per unit length, an increase in the efficiency of light utilization results.

It is believed that the method of the invention proceeds according to the following reaction scheme.

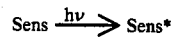

-continued $S_2 +$

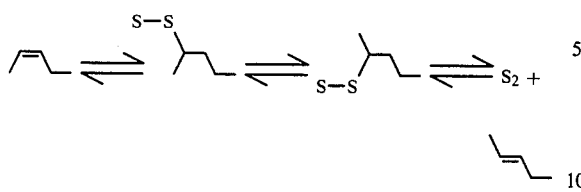

Wherein:
Sens is the photosensitizer,
Sens* is the photosensitizer in an excited or highly energetic state,

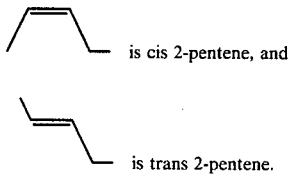 is cis 2-pentene, and

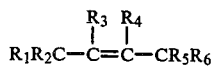 is trans 2-pentene.

It is conventionally thought that the lowest triplet state ($T_1$) of the sensitizer is responsible for the collisional dissociation of COS. It might be assumed that the amount of energy obtained in the triplet state and the light absorption strength of the medium are the only factors involved in determining the effectiveness of a sensitizer. The results of the research leading to the present invention, however, show that this is not the case. For example, conventional aromatic sensitizers such as benzene and toluene are poor sensitizers for the present reaction in spite of the fact that their triplet energies are higher than those of several sensitizers, such as the simple ketones, which are excellent sensitizers for the reaction of the invention.

Olefinic compounds subject to isomerization according to the improved method of the invention include those of the formula:

$$R_1R_2C-\overset{R_3}{\underset{|}{C}}=\overset{R_4}{\underset{|}{C}}-CR_5R_6$$

wherein:
$R_1$, $R_2$, $R_5$ and $R_6$ may be the same or different and are H; OH; straight or branched chain or cyclic alkyl groups having 1–10 carbon atoms, optionally substituted by one or more OH groups; straight or branched chain alkenyl groups having 1–10 carbon atoms, optionally substituted by one or more OH groups, or phenyl, optionally substituted by one or more OH groups;
$R_3$ and $R_4$ are the same or different and are H or straight or branched chain alkyl groups having 1–5 carbon atoms.

The method of the invention is applicable for the conversion of any cis- or tran-isomer of olefinic compounds or mixtures thereof to the photostationary state (PSS) with respect to the ratio of the cis-isomer to the trans-isomer. The PSS of the mixture is the thermodynamic cis/trans equilibrium state of the mixture after irradiation for a time sufficient to achieve a completion of the isomerization reaction. See Schmidt et al, supra. Generally, the PSS of olefinic compounds is such that the ratio of trans-isomer to cis-isomer is well above 1:1.

Accordingly, the method of the invention is best suited for cis-trans isomerization reactions. It will be understood, however, that where there is an excess of trans-isomer over the PSS for a particular mixture, the method will result in a trans-cis isomerization.

The method of particularly applicable for the isomerization of olefins, particularly lower olefins such as 2-pentene and 2-butene. It is to be understood that by the term "lower olefin" is meant those olefinic hydrocarbons having up to 10 carbon atoms.

The method of the invention is also particularly valuable for transforming nerol (the cis-isomer of 3,7-dimethyl-2-6-octadien-1-ol) to the more desirable trans-isomer, namely, geraniol. Nerol and geraniol are valuable commercial products used in perfumes and flavors and as intermediates in the production of other compounds. Although very similar in structure, their sensory and reactive properties differ slightly. Thus, geraniol is currently in much greater demand than nerol. Most geraniol sold commerically is synthesized from pinene. However, present syntheses result in the production of nerol as a major co-product. Typical product ratios are 60:40 geraniol:nerol. For this reason, methods which result in the isomerization of nerol to geraniol are currently of great commercial value. The cis-trans isomerization reaction of the present invention may be carried out by irradiating the reaction mixture at wavelengths of from about 250 to about 400 nm, preferably at wavelengths above about 250 nm.

Any suitable photosensitizer which is capable of absorbing light of wavelengths above about 250 nm and thereafter collisionally dissociating COS to produce the required catalytic species may be utilized in the method of the invention. Preferred photosensitizers include the lower alkanones or phenol. It will be understood that by the term "lower alkanone" is meant alkanones having up to 8 carbon atoms. Particularly preferred photosensitizers include 2-butanone, acetone, methyl isobutyl ketone and phenol.

The isomerization reaction is preferably conducted in the gas phase at temperatures between about 0° and about 300° C. and at pressures between about 1 torr and about 10 atm.

The invention is illustrated by the following non-limiting examples.

EXAMPLE 1

Cis-2pentene is isomerized to trans-2-pentene with COS as a catalyst precursor utilizing the reaction conditions and parameters set forth in Table 1.

TABLE I

| Sensitizer | $T_1{}^a$ | Approximate Vapor Pressure (20° C.) | Isomerization Rate[b] | |
|---|---|---|---|---|
| | | | 266 nm[c] | Xe Lamp[d] |
| None | — | — | 2.5 | 2.8 |
| Acetone | 78 | >100 torr | 4.5[e] | 15[e] |
| 2-Butanone | 78 | 60 | 7.0 | |
| Methyl Isobutyl Ketone | — | 14 | — | 4.2 |
| Acetophenone | 74 | <1 | 1.0 | 2.4 |
| Benzaldehyde | 71.5 | ~1 | — | 2.5 |
| Phenol | 82 | <1 | 4.5 | 6.5 |
| Benzene | 84 | 50 | 1.3 | 3.0 |
| Toluene | 84 | 21 | 1.5 | 3.5 |

TABLE I-continued

| Sensitizer | $T_1{}^a$ | Approximate Vapor Pressure (20° C.) | Isomerization Rate$^b$ 266 nm$^c$ | Xe Lamp$^d$ |
|---|---|---|---|---|
| Pyridine | 85 | 8 | 0.4 | — |

$^a$Triplet energy in kcal/mole
$^b$Rate in torr/min of 50 torr COS + 100 torr cis-2-pentene + sensitizer in 131 cm$^3$ cell
$^c$266 nm 10 Hz 0.17 W pulsed laser
$^d$3 W IR-filtered broadband Xe lamp light
$^e$50 torr acetone used It is evident from the results set forth in Table I that 2-butanone and acetone are particularly effective sensitizers for the cis-trans isomerization reaction. Methyl isobutyl ketone and phenol were less effective but did increase the isomerization rate. Employing broad band Xe lamp radiation as a light source, the addition of 2-butanone at its room temperature vapor pressure to a COS/cis-2-pentene mixture increased the isomerization rate by a factor of 10; a much greater rate than the sum of the rates due to COS and 2-butanone alone. This factor is strong evidence that enhanced catalyst formation is taking place through photosensitization.

Employing 266 nm laser radiation, which is only weakly absorbed by COS, the addition of 2-butanone increased the isomerization rate by a factor of 3. The high overall net efficiency of the method is shown by the fact that the quantum yield under these sensitization conditions is 4. It is thus apparent that the method results in a sensitized production of the required catalyst species leading to a net quantum yield exceeding unity.

EXAMPLE 2

Nerol (0.5 ml) and 0.1 ml of acetone were injected into a sealed vessel containing 750 torr COS at 150° C. and irradiated through a quartz window with 2.3 W of IR-filtered, Xe lamp radiation for 54 minutes. The final solution contaned 50.3% nerol and 49.7% geraniol and no other detectable products. The initial conversion rate was calculated at 11 μl/minute.

EXAMPLE 3

Nerol (0.5 ml) was injected into an evacuated sealed vessel heated to 150° C. and irradiated as in Example 1 for 64 minutes. Result: 73.7% nerol, 26.3% geraniol, initial rate=2.7 μl/minute.

EXAMPLE 4

Nerol (0.5 ml) was injected into an sealed vessel containing 750 torr COS at 150° and irradiated as in Example 1 for 30 minutes. Result=86.8% nerol, 13.2% geraniol, initial rate=2.4 μl/minute.

EXAMPLE 5

Nerol (0.5 ml) and 0.1 ml of acetone were injected into a sealed vessel containing 720 torr $N_2$ at 150° C. and irradiated as in Example 1 for 55 minutes. Result: 80.2% nerol, 19.8% geraniol, initial rate=2.2 μl/minute.

EXAMPLE 6

The reactants and vessel of Example 2 were irradiated with 308 nm pulsed laser light, 100 Hz, 0.14 W, for 16 minutes. Results: 59.6% nerol, 40.4% geraniol, initial rate=22 μl/minute, initial quantum yield=6.

EXAMPLE 7

The reactants and vessel of Example 2 were irradiated with 248 nm pulsed laser light, 10 Hz, 0.14 W, for 25 minutes. Results: 95.7% nerol, 4.3% geraniol, initial rate=0.8 μl/minute, initial quantum yield=0.25.

EXAMPLE 8

The reactants and vessel of Example 3 were irradiated with 248 nm pulsed laser light, 10 Hz, 0.27 W, for 30 minutes. Results: 88.8% nerol, 11.2% geraniol, initial rate=2.0 μl/minute, initial quantum yield=0.34.

The results of Examples 2–8 clearly establish that the method of the invention is a true photosensitized catalytic process. With COS or the acetone sensitizer alone (Examples 4 and 5) the isomerization rate is no greater than the direct photoisomerization rate (Example 3). However, when acetone and COS are combined, the rate is increased (Example 2). Further evidence of the catalytic nature of the process is a relatively high quantum yield ($\phi=6$) obtained with 308 nm laser light. The results of Example 7 show dramatically the importance of the presence of the photosensitizer. Thus, COS is directly excited by 248 nm light; however, nerol is a much stronger absorber than COS 248 nm. Hence, the photons are directly absorbed by nerol and do not contribute to the catalytic reaction. Neither nerol nor COS absorb appreciably at 308 nm; however, the photosensitizer absorption dominates and much of the deposited energy is collisionally transferred to COS. This transfer of energy initiates the catalytic isomerization thereby resulting in the increased isomerization rate.

Presently, nerol is commercially isomerized to geraniol utilizing expensive isomerization catalysts and inefficient methods. The improved method of the present invention enables the efficient isomerization of nerol to geraniol utilizing very inexpensive catalysts. Moreover, the product mixture obtained according to the method of the present invention is more readily separated than those produced according to conventional methods.

It will be understood that any starting material containing cis-olefinic compound may be isomerized according to the present invention. Thus, pure cis-isomer may be isomerized or a mixture of the cis-isomer with the trans-isomer or other compound inert to the reaction conditions may be employed.

I claim:

1. In a method of isomerizing a cis- or trans-olefinic compound or mixture thereof by photoinduced catalysis to the photostationary state with respect to the ratio of the cis-isomer to the trans-isomer wherein the catalytic species capable of catalyzing the isomerization is produced by the indirect photolysis of COS, the improvement comprising effecting the photolysis of COS in the presence of a photosensitizer for the production of said catalytic species, said photosensitizer comprising a compound capable of absorbing light of wavelengths above about 250 nm and thereafter collisionally dissociating COS to produce said catalytic species.

2. The method of claim 1 wherein the starting material contains an excess of cis-olefinic compound over the said photostationary state and said isomerization in a cis-trans isomerization.

3. The method of claim 2 wherein said olefinic compound has the formula:

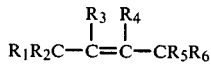

wherein:
R₁, R₂, R₅ and R₆ may be the same or different and are H: OH; straight or branched chain or cyclic alkyl groups having 1-10 carbon atoms, straight or branched chain alkenyl groups having 1-10 carbon atoms, or phenyl;
R₃ and R₄ are the same or different and are H or straight or branched chain alkyl groups having 1-5 carbon atoms.

4. The method of claim 3 wherein said olefinic compound is an olefin.

5. The method of claim 4 wherein said olefin is 2-pentene.

6. The method of claim 4 wherein said olefin is 2-butene.

7. The method of claim 3 wherein said olefinic compound is nerol.

8. The method of claim 5 wherein in said olefinic compound of said formula, said straight or branched chain or cyclic alkyl groups and/or said straight or branched chain alkenyl groups and/or said phenyl group are substituted by one or more OH groups.

9. The method of claim 2 wherein said catalytic species is produced by the photolysis of COS at a wavelength from about 250 to about 400 nm.

10. The method of claim 2 wherein said photosensitizer is alkanone or phenol.

11. The method of claim 10 wherein said photosensitizer is 2-butanone.

12. The method of claim 10 wherein said photosensitizer is acetone.

13. The method of claim 10 wherein said photosensitizer is methyl isobutyl ketone.

14. The method of claim 10 wherein said photosensitizer is phenol.

15. The method of claim 10 conducted at a temperature between about 0° and about 300° C.

16. The method of claim 2 conducted at a pressure between about 1 torr and about 10 atm.

17. A method of effecting cis-trans isomerization of 2-pentene comprising irradiating at a wavelength between about 250 and about 400 nm a mixture comprising an excess of cis-2-pentene over the photostationary state, COS and a photosensitizer comprising a compound capable of absorbing light of wavelengths above about 250 nm and thereafter collisionally dissociating COS to produce a catalytic species capable of catalyzing said cis-trans isomerization.

18. The method of claim 17 wherein said photosensitizer is a lower alkanone or phenol.

19. The method of claim 18 wherein said photosensitizer is acetone, 2-butanone or phenol.

20. The method of claim 18 conducted at a temperature between about 0° and about 300° C.

21. The method of claim 20 conducted at a pressure between about 1 torr and about 10 atm.

22. A method of effecting cis-trans isomerization of nerol to geraniol comprising irradiating at a wavelength between about 250 and about 400 nm a mixture comprising an excess or nerol over the photostationary state, COS and a photosensitizer comprising a compound capable of absorbing light of wavelengths above about 250 nm and thereafter collisionally dissociating COS to produce a catalytic species capable of catalyzing said cis-trans isomerization.

23. The method of claim 22 wherein said photosensitizer is a lower alkanone or phenol.

24. The method of claim 23 wherein said photosensitizer is acetone, 2- butanone or phenol.

25. The method of claim 23 conducted at a temperature between about 100° and about 300° C.

26. The method of claim 25 conducted at a pressure between about 1 torr and about 10 atm.

* * * * *

UNITED STATES PATENT AND TRADEMARK OFFICE
CERTIFICATE OF CORRECTION

PATENT NO. : 4,596,643

DATED : June 24, 1986

INVENTOR(S) : Steven G. Hansen

It is certified that error appears in the above-identified patent and that said Letters Patent is hereby corrected as shown below:

In column 4, at line 6 delete "of" and insert instead --is--.

In column 4, at line 52 delete "Cis-2pentene" and insert instead --Cis-2-pentene--.

In column 4, at line 62 under the colum heading "Xe Lamp$^d$" insert --30--.

In column 8, at line 27 delete "or" and insert instead --of--.

Signed and Sealed this

Ninth Day of December, 1986

Attest:

DONALD J. QUIGG

*Attesting Officer*  *Commissioner of Patents and Trademarks*